(12) United States Patent
Doyle et al.

(10) Patent No.: US 9,498,107 B2
(45) Date of Patent: Nov. 22, 2016

(54) CLAMPING SYSTEM

(75) Inventors: Mark Doyle, Del Mar, CA (US);
Jimmy C. Caputo, Carlsbad, CA (US)

(73) Assignee: CareFusion 2200, Inc., San Diego, CA (US)

( * ) Notice: Subject to any disclaimer, the term of this patent is extended or adjusted under 35 U.S.C. 154(b) by 597 days.

(21) Appl. No.: 12/852,266

(22) Filed: Aug. 6, 2010

(65) Prior Publication Data

US 2012/0035415 A1 Feb. 9, 2012

(51) Int. Cl.
| | |
|---|---|
| *A61B 1/00* | (2006.01) |
| *A61B 5/05* | (2006.01) |
| *A61B 17/00* | (2006.01) |
| *A61B 19/00* | (2006.01) |
| *F16B 1/00* | (2006.01) |

(52) U.S. Cl.
CPC ............ *A61B 1/0014* (2013.01); *A61B 90/50* (2016.02); *A61B 90/57* (2016.02)

(58) Field of Classification Search
USPC ............... 600/104, 106, 115–116, 121–125, 600/156–159, 102, 153–154, 417, 429; 248/74.1, 540, 541, 223.41, 316.6, 62, 248/68.1, 229.1, 229.11–229.17; 403/397; 279/2.02, 55; 362/72, 191, 396; 606/1, 606/130; 604/167.01–167.06
See application file for complete search history.

(56) References Cited

U.S. PATENT DOCUMENTS

| | | | |
|---|---|---|---|
| 594,692 A | 11/1897 | Henneberg | |
| 2,573,325 A * | 10/1951 | Fowlie | ............................ 279/56 |
| 3,539,234 A * | 11/1970 | Rapata | .......................... 384/203 |
| 3,734,513 A * | 5/1973 | Kanebako et al. | ............. 279/48 |
| 3,923,166 A | 12/1975 | Fletcher | |
| 4,414,962 A | 11/1983 | Carson | |
| 4,750,475 A | 6/1988 | Yoshihashi | |
| 5,167,478 A * | 12/1992 | Ramunas | ........................ 279/91 |
| 5,201,908 A | 4/1993 | Jones | |
| 5,361,583 A | 11/1994 | Huitema | |
| 5,441,042 A | 8/1995 | Putman | |
| 5,624,398 A | 4/1997 | Smith et al. | |
| 5,667,185 A * | 9/1997 | Maglica | ........................ 248/541 |
| 5,762,458 A | 6/1998 | Wang et al. | |
| 5,792,135 A | 8/1998 | Madhani et al. | |
| 5,807,240 A | 9/1998 | Muller et al. | |
| 5,807,377 A | 9/1998 | Madhani et al. | |
| 5,808,665 A | 9/1998 | Green | |
| 5,810,712 A * | 9/1998 | Dunn | ..................... A61B 19/26 600/114 |
| 5,855,583 A | 1/1999 | Wang et al. | |
| 5,890,781 A | 4/1999 | Ryder | |
| 5,976,122 A | 11/1999 | Madhani et al. | |
| 6,096,004 A | 8/2000 | Meglan et al. | |

(Continued)

FOREIGN PATENT DOCUMENTS

WO WO-9740759 11/1997

OTHER PUBLICATIONS

ISA/KR, International Search Report and Written Opinion for International Application No. PCT/US2011/046264, 9 pages, Mar. 16, 2012.

*Primary Examiner* — Ryan Henderson

(74) *Attorney, Agent, or Firm* — Arent Fox LLP

(57) ABSTRACT

A collet comprising a cylindrical body comprising a first end and a second end and an aperture coaxial within the cylindrical body. The aperture is configured for receiving a medical device and for securing the medical device by decreasing in diameter when pressure is applied to at least one of the first end and the second end of the cylindrical body.

13 Claims, 3 Drawing Sheets

(56) References Cited

U.S. PATENT DOCUMENTS

| | | |
|---|---|---|
| 6,149,252 A | 11/2000 | Browning |
| 6,301,526 B1 | 10/2001 | Kim et al. |
| 6,364,888 B1 | 4/2002 | Niemeyer et al. |
| 6,554,766 B2 * | 4/2003 | Maeda et al. ............... 600/132 |
| 6,607,475 B2 | 8/2003 | Doyle et al. |
| 7,261,302 B2 * | 8/2007 | Oshnock et al. ............. 279/48 |
| 7,331,967 B2 | 2/2008 | Lee et al. |
| 7,470,268 B2 | 12/2008 | Doyle et al. |
| 7,865,266 B2 | 1/2011 | Moll et al. |
| 8,105,319 B2 | 1/2012 | Doyle et al. |
| 2002/0128633 A1 | 9/2002 | Brock et al. |
| 2004/0049205 A1 | 3/2004 | Lee et al. |
| 2004/0171930 A1 * | 9/2004 | Grimm ............ A61B 17/1703 600/424 |
| 2004/0172041 A1 | 9/2004 | Gresham et al. |
| 2004/0237785 A1 | 12/2004 | Neri |
| 2004/0267089 A1 * | 12/2004 | Otsuka et al. .............. 600/102 |
| 2005/0043718 A1 | 2/2005 | Madhani et al. |
| 2005/0090811 A1 | 4/2005 | Doyle et al. |
| 2005/0169726 A1 | 8/2005 | McClure |
| 2005/0171470 A1 | 8/2005 | Kucklick et al. |
| 2006/0079864 A1 * | 4/2006 | Kronner ............ A61B 19/26 606/1 |
| 2006/0079884 A1 | 4/2006 | Manzo et al. |
| 2006/0161137 A1 | 7/2006 | Orban et al. |
| 2006/0235436 A1 | 10/2006 | Anderson et al. |
| 2007/0123798 A1 | 5/2007 | Rahamimov |
| 2007/0123855 A1 | 5/2007 | Morley et al. |
| 2007/0137371 A1 | 6/2007 | Devengenzo et al. |
| 2007/0156121 A1 | 7/2007 | Millman et al. |
| 2007/0239172 A1 | 10/2007 | Lee et al. |
| 2007/0267026 A1 | 11/2007 | Grant-Jennings |
| 2008/0033453 A1 | 2/2008 | Brock et al. |
| 2008/0065098 A1 | 3/2008 | Larkin |
| 2008/0179839 A1 * | 7/2008 | Walters ..................... 279/51 |
| 2008/0188715 A1 | 8/2008 | Fujimoto |
| 2009/0030443 A1 | 1/2009 | Buser et al. |
| 2009/0105727 A1 | 4/2009 | Doyle et al. |
| 2009/0182351 A1 | 7/2009 | Malinowski |
| 2009/0248039 A1 | 10/2009 | Cooper et al. |
| 2009/0294313 A1 | 12/2009 | Pacey et al. |
| 2010/0063359 A1 | 3/2010 | Okoniewski |
| 2010/0241136 A1 | 9/2010 | Doyle et al. |
| 2011/0178531 A1 | 7/2011 | Caputo et al. |
| 2011/0319911 A1 | 12/2011 | Conner et al. |
| 2012/0010611 A1 | 1/2012 | Krom et al. |
| 2012/0010628 A1 | 1/2012 | Cooper et al. |
| 2012/0083799 A1 | 4/2012 | Chen et al. |
| 2012/0118098 A1 | 5/2012 | Doyle et al. |

* cited by examiner

CLAMPING SYSTEM

BACKGROUND

Many medical devices are sensitive to external forces. The medical devices may be easily damaged if they are not properly handled. For example, it is often necessary to clamp the medical devices during medical procedures. As a result, the medical devices may become damaged due to the clamping forces. Moreover, it may be cumbersome to operate the clamp during the medical procedure.

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Figure 1:
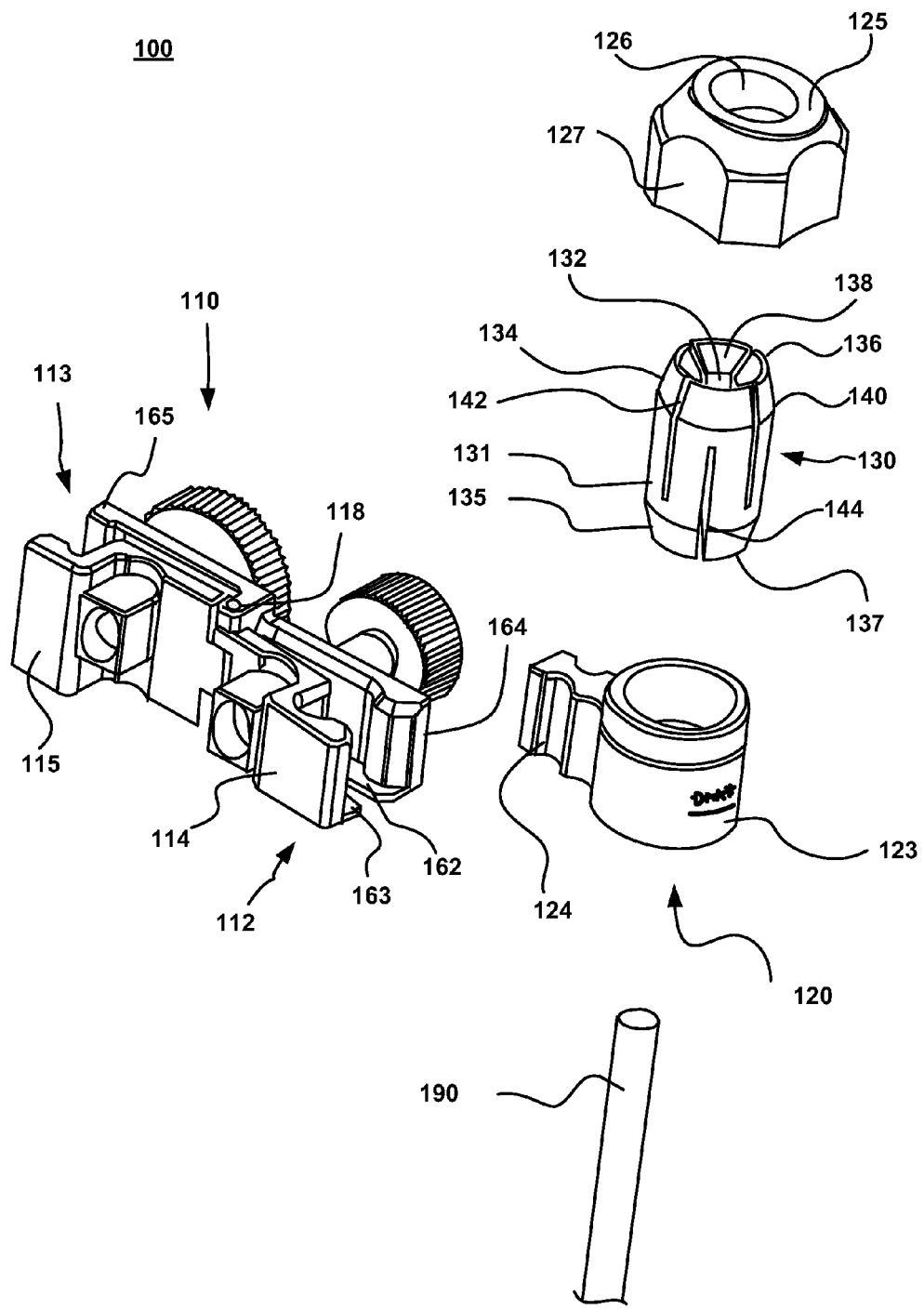
FIG. 1 illustrates an example of an exploded view of a dovetail clamping system, in accordance with an embodiment of the present invention.

FIG. 1 depicts a dovetail clamping system 100, in accordance with an embodiment of the present invention. Dovetail clamping system 100 includes clamping structure 110, collet holder 120 and collet 130.

In general, clamping structure 110 is configured to secure collet holder 120 (and corresponding collet 130) to a supporting structure (e.g., post, bed railing, etc.). Moreover, medical device 190 is received and secured by the combination of collet holder 120 and collet 130. In various embodiment, medical device 190 can be, but is not limited to, an endoscope, cylindrical instruments and laparoscopic instruments.

Collet 130 includes cylindrical body 131 having a first end 136 and a second end 137. Collet 130 also includes aperture 132. Aperture 132 is configured for receiving medical device 190 and for securing medical device 190 by decreasing in diameter when pressure is applied to at least one of first end 136 and second end 137 of cylindrical body 131. In one embodiment, aperture 132 is physically configured to receive an endoscope. The pressure applied to collet 130 is provided by collet holder 120 when lid portion 125 is releasably attached to base portion 123, which will be described in detail below.

In particular, collet 130 includes a compression feature disposed on cylindrical body 131 configured to facilitate in compression of cylindrical body 131 when the pressure is applied to one or more of first end 136 and second end 137. In one embodiment, the compression feature is at least one slot (e.g., slot 140).

As depicted in FIG. 1, collet 130 includes slots 140 and 142 protruding from first end 136 towards second end 137. Slots 140 and 142 extend the diameter of cylindrical body 131 and are orthogonal to one another.

Similarly, collet 130 also includes two slots protruding from second end 137 towards first end 136. One such slot is slot 144. The other slot (not depicted) is orthogonal to slot 144.

In various embodiments, collet 130 can include any number of compression features (e.g., slots) in any orientation that facilitates in the compression of cylindrical body 131.

Collet 130 includes first outer chamfer 134 and second outer chamfer 135. First out chamfer 134 and second outer chamfer 135 are configured for facilitating in the decreasing of the diameter of aperture 132 when the pressure is applied to either first out chamfer 134 or second outer chamfer 135. For example, pressure is applied to first out chamfer 134 and second outer chamfer 135 by collet holder 120, when lid portion 125 is attached to base portion 123, which will be described in detail below.

Figure 2:
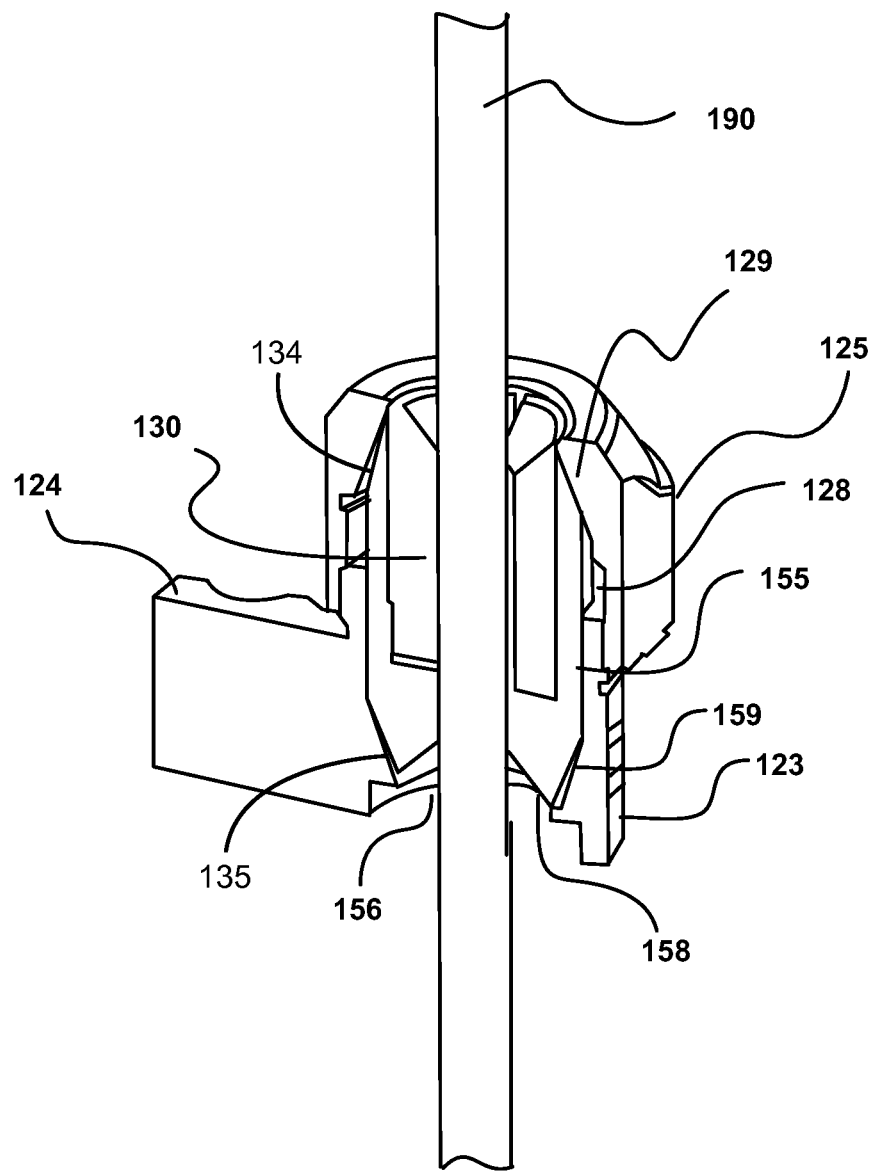
FIG. 2 illustrates an example of a collet holder and collet, in accordance with an embodiment of the present invention.

FIG. 2 depicts a cross-sectional view of medical device 190 received and secured by the combination of collet holder 120 and collet 130, in accordance to an embodiment of the present invention. Referring to both FIGS. 1 and 2, collet holder 120 includes base portion 123, lid portion 125 and dovetail interface 124.

Dovetail interface 124 is configured to be received by first dovetail clamp 112 depicted in FIGS. 1 and 3, which will be described in detail below. In various embodiments, dovetail interface 124 is coupled to one of lid portion 125 and base portion 123.

Lid portion 125 includes lid aperture 126, lid cavity 128 and lid chamfer 129. Similarly, base portion 123 includes base aperture 156, base cavity 155 and base chamfer 159. Lid cavity 128 and base cavity 155 are configured for receiving collet 130. Lid aperture 126 and base aperture 156 are configured for receiving medical device 190.

Lid portion 125 is releasably coupled to base portion 123. In one embodiment, lid portion 125 is releasably coupled to base portion 123 via screw threads. In one embodiment, lid portion 125 includes features 127 configured for enhancing the gripping of lid portion 125 for releasably coupling lid portion 125 to base portion 123.

When lid portion 125 is coupled to base portion 123, pressure is applied to first end 136 and second end 137 of collet 130. As a result, collet 130 is compressed. Thus, medical device 190 is retained within collet 130.

Specifically, when lid portion 125 is coupled to base portion 123, pressure is applied by lid chamfer 129 to first outer chamfer 134. Likewise, pressure is also applied by base chamfer 159 to second outer chamfer 135. As a result, collet 130 is compressed. Thus, medical device 190 is sufficiently retained within collet 130 without damaging medical device 190.

Collet 130 also includes first inner chamfer 138 and second inner chamfer 158. First inner chamfer 138 and second inner chamfer 158 are configured to reduce stresses at the region of bending of medical device 190.

Figure 3:
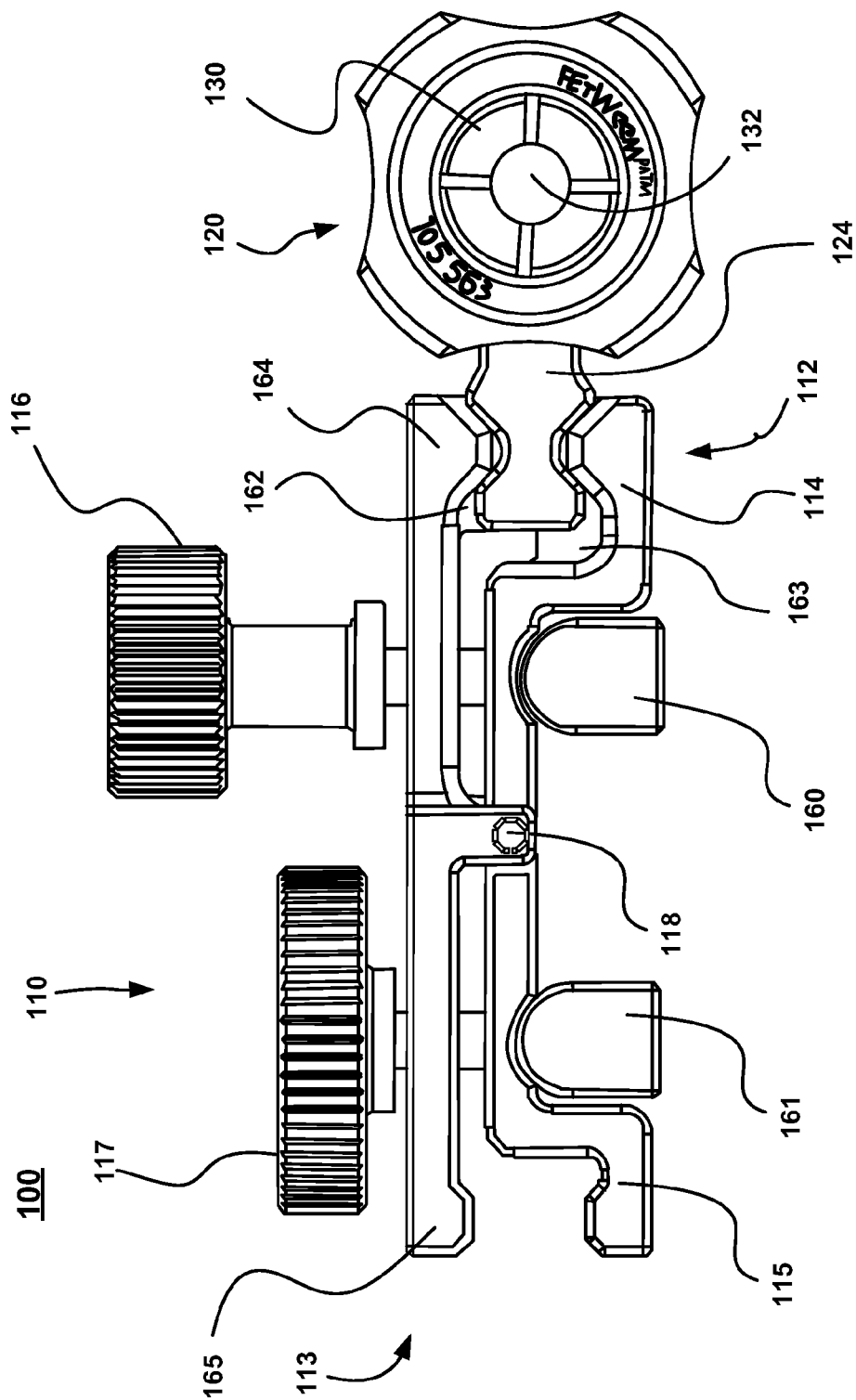
FIG. 3 illustrates an example of a dovetail clamping system, in accordance with an embodiment of the present invention.

FIG. 3 depicts a dovetail clamping system 100, in accordance with an embodiment of the present invention. Dovetail clamping system 100 includes clamping structure 110, collet holder 120 and collet 130, as described above. In one embodiment, clamping structure 110 and collet holder 120 are a single unitary clamping structure (rather than separate structures, as depicted).

Referring to FIGS. 1 and 3, clamping structure 110 includes first dovetail clamp 112, second dovetail clamp 113, first actuator 116 and second actuator 117.

First dovetail clamp 112 is configured for receiving and securing first dovetail interface 124. First dovetail clamp 112 is further configured for single handed operation by a user, which will be described in detail below. First dovetail clamp 112 includes first rotatable jaw 114, first fixed jaw 164, first actuator 116, first shelf 162 and second shelf 163.

Second dovetail clamp 113 is configured to clamp to a corresponding second dovetail interface (not shown). In various embodiments, second dovetail clamp 113 is configured to clamp to any stable structure such as, but not limited to, a post, bed rail, etc. Second dovetail clamp 113 includes second rotatable. jaw 115, second fixed jaw 165 and second actuator 117. Second dovetail clamp 113 faces opposite first dovetail clamp 112.

It should be appreciated that clamping structure 110 can include any clamping or connection mechanism (other than dovetail clamps), such as but not limited to, a vice. Likewise, first dovetail interface 124 and second dovetail interface can be any clamping or mechanical connection interface.

In various embodiments, first actuator 116 and second actuator 117 are thumb screws. For example, as a user rotates second actuator 117, second rotatable jaw 115 rotates with respect to hinge 118. In particular, as second actuator 117 is rotated, second nut 161 is drawn closer to thumb screw 117. As a result, second rotatable jaw 115 rotates towards second fixed jaw 165 and a corresponding second dovetail interface is clamped in second dovetail clamp 113.

Similarly, as first actuator 116 is rotated by a single hand of a user, first rotatable jaw 114 rotates with respect to hinge 118. In particular, as first actuator 117 is rotated, first nut 160 is drawn closer to first actuator 116. As a result, first rotatable jaw 114 rotates towards first fixed jaw 164 and corresponding first dovetail interface 124 is clamped in first dovetail clamp 112.

Moreover, first fixed jaw 164 and second fixed jaw 165 include first shelf 162 and second shelf 163, respectively, to facilitate in the placement of first dovetail interface 124 between first fixed jaw 164 and first rotatable jaw 114. For example, first dovetail interface 124 may be placed into position between first rotatable jaw 114 and first fixed jaw 164 and on first shelf 162 and second shelf 163 by a single hand of the user. Once in place, first dovetail interface can be clamped into first dovetail clamp 112, as described above.

Various embodiments of the present invention are thus described. While the present invention has been described in particular embodiments, it should be appreciated that the present invention should not be construed as limited by such embodiments, but rather construed according to the following claims.

The invention claimed is:

1. A clamping system comprising:
a collet comprising:
a cylindrical body comprising a first end and a second end;
an aperture coaxial within said cylindrical body, wherein said aperture is configured for receiving and securing a medical device by decreasing in diameter when pressure is applied to at least one of said first end and said second end of said cylindrical body;
a first outer chamfer disposed at said first end, wherein said first outer chamfer is configured for facilitating in said decreasing in said diameter of said aperture when said pressure is applied to said first outer chamfer;
a second outer chamfer disposed at said second end, wherein said second outer chamfer is configured for facilitating in said decreasing in said diameter of said aperture when said pressure is applied to said second outer chamfer; and
a first inner chamfer disposed at said first end, wherein said first inner chamfer is configured for reducing stress at a region of bending of the medical device;
a collet holder comprising:
a lid portion comprising a lid cavity for receiving the collet;
a base portion having a circumferential surface, the base portion comprising a cylindrical base cavity for receiving said collet, wherein said pressure is applied to said collet when said lid portion is releasably coupled to said base portion, and wherein said collet is configured for receiving said medical device and securing said medical device when said pressure is applied to said collet; and
a clamping interface extending radially from the circumferential surface of the base portion, the clamping interface comprising:
a first mating surface; and
a second mating surface, the first mating surface opposing the second mating surface; and
a clamping structure comprising a first jaw and a second jaw, the second jaw opposing the first jaw,
wherein the first jaw is configured to mate with the first mating surface of the clamping interface and the second jaw is configured to mate with the second mating surface of the clamping interface such that the clamping interface is retained between the first and second jaws.

2. The clamping system of claim 1, wherein said first mating surface comprises a first dovetail interface.

3. The clamping system of claim 2, wherein said first jaw comprises a second dovetail interface for mating with the first dovetail interface.

4. The clamping system of claim 1, and wherein the clamping structure is configured for single handed operation by a user.

5. The clamping system of claim 1, wherein the clamping structure comprises a third jaw, and wherein the first jaw and the third jaw rotate about a single hinge.

6. The clamping system of claim 1, wherein said collet holder is configured for receiving and securing an endoscope.

7. The clamping system of claim 1, wherein said collet comprises a compression feature disposed on said cylindrical body configured to facilitate in compression of said cylindrical body when said pressure is applied to one or more of said first end and said second end of said cylindrical body.

8. The clamping system of claim 7, wherein said compression feature comprises: at least one slot longitudinally disposed along said cylindrical body.

9. The dovetail clamping system of claim 1, wherein said lid portion comprises a lid chamfer configured to apply said pressure to said first outer chamfer of said collet to facilitate in compression of said collet.

10. The dovetail clamping system of claim 9, wherein said base portion comprises a base chamfer configured to apply said pressure to said second outer chamfer of said collet to facilitate in compression of said collet.

11. The clamping system of claim 1, wherein said lid portion is releasably coupled to said base portion by corresponding screw threads disposed on said lid portion and said base portion.

12. The clamping system of claim 1, wherein the first mating surface comprises a first dovetail interface, the second mating surface comprises a second dovetail interface, the first jaw comprises a third dovetail interface, the second jaw comprises a fourth dovetail interface, the first dovetail interface is configured to mate with the third dovetail interface, and the second dovetail interface is configured to mate with the fourth dovetail interface.

13. The clamping system of claim 12, wherein the first jaw is moveable relative to the second jaw.

\* \* \* \* \*